United States Patent [19]

Au

[11] Patent Number: 4,546,189

[45] Date of Patent: Oct. 8, 1985

[54] PREPARATION OF CYANO(6-(SUBSTITUTED PHENOXY)-2-PYRIDINYL)METHYL ESTERS OF 3-(2,2-DIHALOETHENYL)-2,2-DIMETHYL-CYCLOPROPANE CARBOXYLIC ACIDS

[75] Inventor: Andrew T. Au, Needham, Mass.

[73] Assignee: The Dow Chemical Company, Midland, Mich.

[21] Appl. No.: 484,083

[22] Filed: Apr. 11, 1983

Related U.S. Application Data

[63] Continuation-in-part of Ser. No. 350,521, Feb. 19, 1982, abandoned, which is a continuation-in-part of Ser. No. 199,392, Oct. 23, 1980, abandoned.

[51] Int. Cl.$^4$ ............................................. C07D 213/64
[52] U.S. Cl. ..................................................... 546/300
[58] Field of Search ........................................ 546/300

[56] References Cited

U.S. PATENT DOCUMENTS

| | | | |
|---|---|---|---|
| 4,163,787 | 8/1979 | Malhotra et al. | 424/263 |
| 4,215,138 | 7/1980 | Ozawa et al. | 424/282 |
| 4,221,799 | 9/1980 | Van Heertum et al. | 546/300 |
| 4,228,172 | 10/1980 | Malhotra et al. | 424/263 |
| 4,254,050 | 3/1981 | Baum | 260/465 D |
| 4,254,051 | 3/1981 | Baum | 260/465 |
| 4,254,052 | 3/1981 | Baum | 260/465 D |
| 4,264,606 | 4/1981 | Ozawa et al. | 546/300 |
| 4,315,012 | 2/1982 | Martel et al. | 546/300 |
| 4,323,685 | 4/1982 | Baum | 546/300 |

*Primary Examiner*—Ethel G. Love
*Attorney, Agent, or Firm*—S. Preston Jones; Ronald G. Brookens

[57] ABSTRACT

The present application is directed to a process for preparing cyano(6-(substituted phenoxy)-2-pyridinyl)-methyl esters of 3-(2,2-dihaloethenyl)-2,2-dimethylcyclopropane carboxylic acids wherein an appropriate 6-(substituted phenoxy)picolinaldehyde is reacted with a 3-(2,2-dihaloethenyl)-2,2-dimethylcyclopropane carboxylic acid anhydride or halide in the presence of an aqueous alkali metal cyanide and an organic solvent.

8 Claims, No Drawings

_4,546,189_

PREPARATION OF CYANO(6-(SUBSTITUTED PHENOXY)-2-PYRIDINYL)METHYL ESTERS OF 3-(2,2-DIHALOETHENYL)-2,2-DIMETHYLCYCLOPROPANE CARBOXYLIC ACIDS

CROSS-REFERENCE TO RELATED APPLICATION

This is a continuation-in-part of application Ser. No. 350,521, filed Feb. 19, 1982, now abandoned, which in turn is a continuation-in-part of application Ser. No. 199,392, filed Oct. 23, 1980, now abandoned.

BACKGROUND OF THE INVENTION

In U.S. Pat. No. 4,163,787, cyano(6-(substituted pyridinyl)methyl esters of 3-(2,2-dihaloethenyl)-2,2-dimethylcyclopropane carboxylic acids, their preparation and their utility as insecticides are taught. One of the drawbacks to the commercial use of these compounds is the cost of their preparation.

In the patent, the compounds are prepared by the reaction of an appropriate cyano(6-(substituted phenoxy)-2-pyridine)methanol with a 3-(2,2-dihaloethenyl)-2,2-dimethylcyclopropane carboxylic acid halide in the presence of a solvent and a hydrogen halide acceptor.

The pyridine methanol reactant is prepared by the reaction, at room temperature, of an appropriate 6-(substituted phenoxy)picolinaldehyde with an excess of an alkali metal cyanide in the presence of an alkali metal bisulfite and water. While the process as taught by U.S. Pat. No. 4,163,787 gives the desired product, other more economical methods of preparation are being sought.

SUMMARY OF THE INVENTION

The present invention is directed to a process for preparing cyano(6-(substituted phenoxy)-2-pyridinyl)methyl esters of 3-(2,2-dihaloethenyl)-2,2-dimethylcyclopropane carboxylic acids. These compounds correspond to the formula

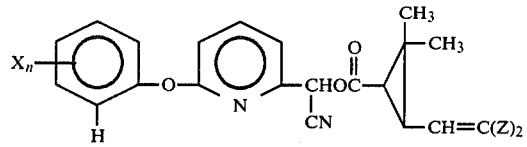

wherein X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; n represents an integer of 0 to 2 and Z represents chloro, fluoro or bromo.

In the present process, an appropriate 6-(substituted phenoxy)picolinaldehyde is reacted with a 3-(2,2-dihaloethenyl)-2,2-dimethylcyclopropane carboxylic acid anhydride or halide (chloride, bromide or fluoride) in substantially equimolar proportions in the presence of an aqueous alkali metal cyanide and an organic solvent, with or without the additional presence of a catalyst.

The reaction scheme can be characterized as follows:

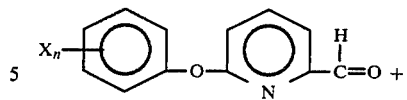

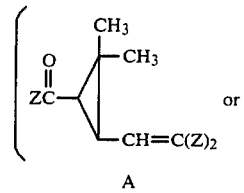

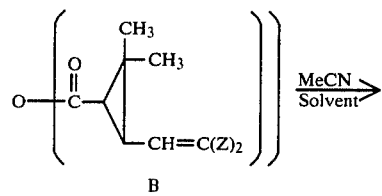

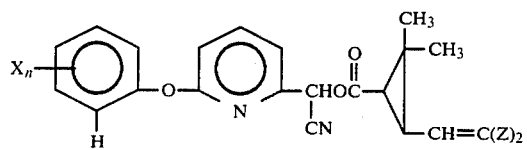

wherein Me is sodium, potassium, lithium or cesium and Z, X and n are as herein above defined. No attempt has been made to present a balanced equation.

In carrying out this process, the aldehyde and acid halide (or anhydride) reactants are mixed together in an organic non-polar solvent such as, for example, carbon tetrachloride, methylene chloride, toluene or chloroform.

This mixture is then admixed with an aqueous alkali metal cyanide solution. Representative cyanides include the cyanides of sodium, potassium, lithium and cesium with sodium cyanide being preferred considering the relative costs of the different cyanides. It has been found that the reaction rate is aided by the use of excess cyanide and it is preferred that from 1.5 to 2.0 molar equivalents of the cyanide be employed although amounts of from 1 to 10 molar equivalents can be used.

The process proceeds well with or without the presence of a catalyst. The main advantage in the use of a catalyst is in the slight increase in the reaction rate in the production of the desired compound.

If it is decided to use a catalyst, essentially any compound from the known class of quaternary ammonium and phosphonium salts can be employed. Suitable quaternary ammonium and phosphonium salts have a minimum solubility of at least about 1 weight percent in the liquid reaction medium at 25° C. and normally have a total aggregate carbon content of at least about 10 carbon atoms and preferably from about 12 to about 31 carbon atoms. The ammonium and phosphonium salts can be represented by the formula

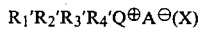

wherein $R_1'-R_4'$ are hydrocarbyl groups (e.g., alkyl, aryl, alkaryl, aralkyl, cycloalkyl, etc.) and $Q^\oplus$ is a quaternized atom or nitrogen or phosphorus. Additionally, in (X)$R_1'$ can join with $R_2'$ to form a 5- or 6-membered heterocyclic compound having at least one quaternized nitrogen or phosphorus atom in the ring and may also contain one non-adjacent atom of nitrogen, oxygen or sulfur within the ring. Typically $R_1'-R_4'$ in (X) are hydrocarbyl groups of from 1 to about 12 carbon atoms. $A^\ominus$ is an inert neutralizing anion and may be varied to convenience. By "inert" is meant inert in the instant process. Chloride and bromide are the preferred anions but other suitable anions include for example fluoride, bisulfate, hydroxide, perchlorate, nitrate, tosylate and the like. The following compounds are illustrative: tetraalkyl ammonium salts, such as tetra-n-butyl-, tetrahexyl-, tri-n-butylmethyl-, cetyltrimethyl-, trioctylmethyl- and tridecylmethyl ammonium chlorides, bromides, bisulfates, tosylates, etc.; aralkylammonium salts, such as tetrabenzylammonium chloride, benzyltrimethyl-, benzyltriethyl-, benzyltributyl-, and phenethyltrimethyl- ammonium chlorides, bromides, etc.; arylammonium salts, such as triphenylmethylammonium fluoride, chloride or bromide N,N,N-trimethylanilinium bromide, N,N-diethyl-N-methylanilinium bisulfate, trimethylnaphthylammonium chloride, p-methylphenyltrimethylammonium chloride or tosylate, etc.; 5- and 6-membered heterocyclic compounds containing at least one quaternized nitrogen atom in the ring, such as N-methylpyridinium chloride or methyl sulfate, N-hexyl pyridinium iodide. (4-pyridyl)-trimethylammonium chloride, 1-methyl-1-azabicyclo[2.2.1]heptane bromide, N,N-dibutylmorpholinium chloride, N-ethylthiazolium chloride, N-butylpyrrolium chlorides, etc., and the corresponding phosphonium salts and other like compounds.

The ammonium salts are currently preferred over the phosphonium salts due to cost and commercial availability. The most preferred catalysts are benzyltrimethyl-, benzyltriethyl-, tetra-n-butyl and tri-n-butylmethyl ammonium salts.

The quaternary ammonium and phosphonium salts are used in the process in small but catalytic amounts. For example, amounts from about 0.1 to about 20 mole percent, based on the reactants, are suitable but amounts of from about 0.5 to about 10 mole percent are generally preferred.

The reaction is carried out in the absence of a catalyst and can be conducted over a wide temperature range such as, for example, from about $-30°$ to about $100°$ C. It is preferred to employ temperatures of from about $-20°$ C. to about room temperature.

The reaction is usually complete in from about 2 to 5 hours, depending upon the reaction. However, times of from about 1 hour to several days can be employed without overly affecting the formation of the desired product.

The reaction produces as a by-product a tar which must be removed as a part of the purification procedures. The amount of tar produced can be controlled to some extent by the selection of the solvent and to a lesser extent by the selection of temperature.

At the completion of the reaction, the desired product can be separated from the tar by extracting it from the reaction mixture with a solvent such as, for example, light petroleum ether. The product can then be separated from the ether by conventional separatory techniques such as decantation, distillation and evaporation.

Alternatively, the tar can be conveniently removed by passing the reaction mixture through a fixed bed of an adsorbent such as, for example, silica gel, alumina or charcoal.

EXAMPLE I

Preparation of 3-(2,2-dichloroethenyl)-2,2-dimethylcyclopropane carboxylic acid:cyano-(6-phenoxy-2-pyridinyl)methyl ester

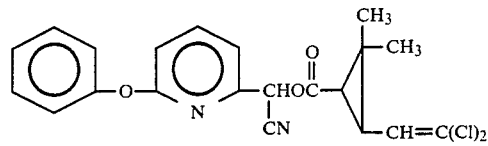

To a mixture of 5.0 grams (0.1 mole) of sodium cyanide in 25 milliliters of water at room temperature was added over a 15 minute period, with stirring, 50 milliliters of toluene containing 10.3 grams (0.052 mole) of 6-(phenoxy)picolinaldehyde and 11.35 grams (0.05 mole) of 3-(2,2-dichloroethenyl)-2,2-dimethylcyclopropane carboxylic acid chloride. A mild exotherm developed during the addition and the mixture was cooled to room temperature on a water bath. The mixture was stirred for four hours at room temperature. The organic phase was separated, washed with a saturated sodium bisulfite solution, then with a sodium bicarbonate solution. The reaction mixture was then dried and then passed through a sinter glass funnel containing 65 grams of silica gel. The filtrate was concentrated to yield 21.0 grams of a pale yellow viscous oil.

EXAMPLE II

Preparation of 3-(2,2-dichloroethenyl)-2,2-diemthylcyclopropane carboxylic acid:cyano-(6-phenoxy-2-pyridinyl)methyl ester To a mixture of 5.0 grams (0.1 mole) of sodium cyanide in 25 milliliters of water at room temperature was added over a 15 minute period, with stirring, 50 milliliters of toluene containing 10.3 grams (0.052 mole) of 6-(phenoxy)picolinaldehyde and 11.35 grams (0.05 mole) of 3-(2,2-dichloroethenyl)-2,2-dimethylcyclopropane carboxylic acid chloride. A mild exotherm developed during the addition and the mixture was cooled to room temperature on a water bath. The mixture was stirred for four hours at room temperature. The organic phase was separated, washed with a saturated sodium bisulfite solution, then with a sodium bicarbonate solution. The reaction mixture was then dried and then passed through a sinter glass funnel containing 65 grams of silica gel. The filtrate was concentrated to yield 21.0 grams of a pale yellow viscous oil.

In the above examples, the structure of the compound was confirmed by both the infrared and nuclear magnetic resonance spectra thereof. It was further noted that the purity of the product was at least 90 percent.

By following the preparative procedures, as outlined above, employing the appropriate reactants, other compounds of Formula I can be prepared.

What is claimed is:

1. A process for preparing cyano(6-(substituted phenoxy)-2-pyridinyl)methyl esters of 3-(2,2-dihaloethenyl)-2,2-dimethylcyclopropane carboxylic acids corresponding to the formula

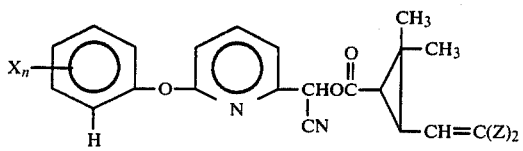

wherein X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo; n represents an integer of 0 to 2 and Z represents chloro, fluoro or bromo which comprises reacting a 6-(substituted phenoxy)picolinaldehyde with a 3-(2,2-dihaloethenyl)-2,2-dimethylcyclopropane carboxylic acid anhydride or halide in the presence of an aqueous alkali metal cyanide solution and an organic solvent.

2. A process as defined in claim 1 wherein the 6-(substituted phenoxy)picolinaldehyde and the 3-(2,2-dihaloethenyl)-2,2-dimethylcyclopropanol carboxylic acid anhydride or halide reactants are employed in substantially equimolar proportions.

3. The process as defined in claim 2 wherein the 3-(2,2-dihaloethenyl)-2,2-dimethylcyclopropane carboxylic acid halide reactant is in the form of the carboxylic acid chloride.

4. The process as defined in claim 3 wherein the alkali metal cyanide reactant is sodium cyanide.

5. The process as defined in claim 4 wherein from 1.5 to 2.0 molar equivalents of the sodium cyanide is employed.

6. The process as defined in claim 5 wherein the reaction is conducted at a temperature in the range of from about $-30°$ to about $100°$ C.

7. The process as defined in claim 6 wherein the reaction is conducted at a temperature in the range of from about $-20°$ C. to about room temperature.

8. The process as defined in claim 7 wherein 6-(phenoxy)picolinaldehyde is reacted with 3-(2,2-dichloroethenyl)-2,2-dimethylcyclopropane carboxylic acid chloride and the product is 3-(2,2-dichloroethenyl)-2,2-dimethylcyclopropane carboxylic acid:-cyano-(6-phenoxy-2-pyridinyl)methyl ester.

* * * * *